United States Patent
Jugl et al.

(10) Patent No.: US 10,272,204 B2
(45) Date of Patent: Apr. 30, 2019

(54) DRUG DELIVERY DEVICE AND METHOD FOR ELECTRICALLY DETECTING CONTACT BETWEEN PISTON ROD AND CARTRIDGE BUNG

(71) Applicant: Sanofi-Aventis Deutschland GmbH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/421,410

(22) PCT Filed: Aug. 15, 2013

(86) PCT No.: PCT/EP2013/067061
§ 371 (c)(1),
(2) Date: Feb. 12, 2015

(87) PCT Pub. No.: WO2014/029683
PCT Pub. Date: Feb. 27, 2014

(65) Prior Publication Data
US 2015/0217060 A1 Aug. 6, 2015

(30) Foreign Application Priority Data
Aug. 20, 2012 (EP) .................................... 12180962

(51) Int. Cl.
*A61M 5/315* (2006.01)
*A61M 5/31* (2006.01)
(Continued)

(52) U.S. Cl.
CPC ...... *A61M 5/31515* (2013.01); *A61M 5/3146* (2013.01); *G01R 27/02* (2013.01);
(Continued)

(58) Field of Classification Search
CPC ............ A61M 5/31515; A61M 5/3146; A61M 2205/12; A61M 2205/332;
(Continued)

(56) References Cited

U.S. PATENT DOCUMENTS

| 533,575 A | 2/1895 | Wilkens |
| 5,226,895 A | 7/1993 | Harris |

(Continued)

FOREIGN PATENT DOCUMENTS

| CN | 1816363 A | 8/2006 |
| CN | 101111281 A | 1/2008 |

(Continued)

OTHER PUBLICATIONS

Robert C. Faber, Faber on Mechanics of Patent Claim Drafting, Sixith Edition, Practicing Law Institute, Copyright 2012, p. 4-2.*
(Continued)

*Primary Examiner* — Amber Stiles
(74) *Attorney, Agent, or Firm* — McCarter & English, LLP

(57) ABSTRACT

The present invention is directed to a drug delivery device comprising a cartridge with a movable bung, a drive mechanism including a bearing for driving the bung in a distal direction for delivering a medicament and a piston rod for actuating the bearing. An electric conductor for transmitting an electrical signal is provided, wherein the electric conductor is configured such that a conductive connection is established or interrupted when the piston rod contacts the bearing or when the bearing contacts the bung. The invention is further directed to a method for detecting the contact between the drive mechanism and the movable bung.

10 Claims, 2 Drawing Sheets

(51) Int. Cl.
  *G01R 27/02*    (2006.01)
  *G01V 3/00*    (2006.01)
(52) U.S. Cl.
  CPC ............ *G01V 3/00* (2013.01); *A61M 2205/12* (2013.01); *A61M 2205/332* (2013.01); *A61M 2205/3306* (2013.01); *A61M 2205/3317* (2013.01); *A61M 2205/3327* (2013.01); *A61M 2205/3375* (2013.01); *A61M 2205/581* (2013.01); *A61M 2205/583* (2013.01); *A61M 2205/6027* (2013.01); *A61M 2207/00* (2013.01); *Y10T 29/49764* (2015.01)
(58) Field of Classification Search
  CPC .. A61M 2205/3327; A61M 2205/3306; A61M 2205/6027; A61M 2205/3317; A61M 2205/583; A61M 2205/581; A61M 2207/00; A61M 2205/3375; G01V 3/00; G01R 27/02; Y10T 29/49764
  See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 8,398,588 B1 | 3/2013 | Lampropoulos et al. | |
| 8,544,645 B2 | 10/2013 | Edwards et al. | |
| 8,926,553 B2 | 1/2015 | Langley et al. | |
| 9,610,407 B2 | 4/2017 | Bruggemann et al. | |
| 9,910,407 B2 | 3/2018 | Kakutani et al. | |
| 2001/0034506 A1* | 10/2001 | Hirschman | A61M 5/14546 604/207 |
| 2002/0052578 A1 | 5/2002 | Moller | |
| 2002/0120235 A1 | 8/2002 | Enggaard | |
| 2003/0050609 A1 | 3/2003 | Sams | |
| 2004/0024364 A1 | 2/2004 | Langley et al. | |
| 2004/0059299 A1 | 3/2004 | Moller | |
| 2004/0158205 A1 | 8/2004 | Savage | |
| 2004/0210199 A1 | 10/2004 | Atterbury et al. | |
| 2004/0267207 A1* | 12/2004 | Veasey | A61M 5/24 604/208 |
| 2005/0113765 A1 | 5/2005 | Veasey et al. | |
| 2006/0153693 A1 | 7/2006 | Fiechter et al. | |
| 2009/0275916 A1 | 11/2009 | Harms et al. | |
| 2010/0094222 A1* | 4/2010 | Grant | A61M 5/1456 604/151 |
| 2010/0211005 A1* | 8/2010 | Edwards | A61M 5/002 604/82 |
| 2010/0217188 A1* | 8/2010 | Lampropoulos | A61M 25/1018 604/97.03 |
| 2010/0256486 A1 | 10/2010 | Savage | |
| 2012/0071819 A1* | 3/2012 | Bruggemann | A61M 5/14546 604/67 |

FOREIGN PATENT DOCUMENTS

| | | |
|---|---|---|
| CN | 102245257 A | 11/2011 |
| EP | 0937471 A2 | 8/1999 |
| EP | 0937476 A2 | 8/1999 |
| EP | 1974761 A2 | 10/2008 |
| GB | 190226674 | 10/2003 |
| JP | 59-120164 A | 7/1984 |
| JP | 2002-518108 A | 6/2002 |
| JP | 2004-516106 A | 6/2004 |
| JP | 2012-516737 A | 7/2012 |
| WO | 9938554 A1 | 8/1999 |
| WO | 9965548 A1 | 12/1999 |
| WO | 0110484 A1 | 2/2001 |
| WO | 03101527 A1 | 12/2003 |
| WO | 2004/078240 A2 | 9/2004 |
| WO | 2008105952 A2 | 9/2008 |
| WO | 2011036133 A1 | 3/2011 |

OTHER PUBLICATIONS

American Heritage Dictionary Definition for "Application". Definitions 1, 2 and 4, available online as of Feb. 26, 2016 at https://www.ahdictionary.com/word/search.html?q=application.*
Merriam-Webster Dictionary Definition of "Electrical". Definition 1, available online as of Feb. 26, 2016 at http://www.merriam-webster.com/dictionary/electrical.*
Office Action issued in Chinese Patent Application No. 201380042917.1 dated Oct. 9, 2016.
English Translation of Description and Claims of Japanese Patent Application No. 59-120164 dated Jul. 20, 2017.
Communication pursuant to Article 94/(3) EPC issued in European Patent Application No. 10713891.9 dated Oct. 5, 2017.

\* cited by examiner

DRUG DELIVERY DEVICE AND METHOD FOR ELECTRICALLY DETECTING CONTACT BETWEEN PISTON ROD AND CARTRIDGE BUNG

CROSS REFERENCE TO RELATED APPLICATIONS

The present application is a U.S. National Phase application pursuant to 35 U.S.C. § 371 of International Application No. PCT/EP2013/067061 filed Aug. 15, 2013, which claims priority to European Patent Application No. 12180962.8 filed Aug. 20, 2012. The entire disclosure contents of these applications are herewith incorporated by reference into the present application.

FIELD OF INVENTION

The present invention is directed at a drug delivery device comprising a cartridge with a movable bung, a drive mechanism including a bearing for driving the bung in a distal direction for delivering a medicament such as insulin and a piston rod for actuating the bearing. The invention is further directed at a method for detecting a contact between the drive mechanism and the movable bung.

BACKGROUND

Pen type drug delivery devices have applications where regular injection by persons without formal medical training occurs. This is increasingly common among patients having diabetes or the like. Self-treatment enables such patients to conduct effective management of their disease. The injection pens usually comprise a housing in which the drive mechanism is located. Some kinds of drug delivery devices also comprise a compartment to accommodate a cartridge in which the medicament is received. With the drive mechanism, the bung in the cartridge is displaced for dispensing the medicament accommodated therein. The drive mechanism includes a piston rod that has a bearing at one end, wherein the bearing is arranged in such manner such that it faces the bung. With the piston rod, the bearing is displaced toward the bung and urges the bung toward a distal end of the drug delivery device, which is closest to the dispensing end (needle end) of the device. Medicament from the cartridge is dispensed thereby. The opposite side of the device is referred to as the proximal end.

In devices of the generic kind, the manufacture may bring unavoidable tolerances and functional clearances between the single components of the drug delivery device, in particular the drive mechanism. As a consequence, clearances such as a gap between the elements of the drive mechanism, such as between the bearing and the cartridge bung may occur even after the drug delivery device has been assembled so that the bung may not be in contact with the distal end of the bearing. It is, therefore, important to eliminate the gap between the cartridge bung and the distal end of the bearing and to bring the drive mechanism in a prestressed state prior to use. Otherwise, it is possible that the dialed dose may not be dispensed from the device correctly. Initial clearances may already falsify the setting of the dose. To adjust the drug delivery device for use, priming actions are conducted to ensure that the drive mechanism is correctly adjusted, e.g. that the drive mechanism is in contact with the bung so that the correct amount of the medicament can expelled from the device. These actions often come along with a small amount of medicament being dispensed which gives a visual indication that the drug delivery device is ready to use.

It is known in the art to conduct adjustment of the drug delivery device by measurement of the bearing and the bung position before pressing, resp. assembly. The parts are then adjusted according to the measured value such that the bearing is brought into contact with the bung. However, the assembly machines for this method are expensive and the required time cycle is very long.

SUMMARY

It is an object of the present invention to simplify the adjustment process in a drug delivery device. This object is solved by a drug delivery device as defined by claim 1 and by a method for detecting a contact between the drive mechanism and the bung as defined in claim 12.

With the measures provided by the invention, an electrical signal or the like can be used to indicate, when the drive mechanism is connected to the bung as intended. It is, for example, possible, to use an electric, i.e. an electric circuit, which is closed or interrupted by establishing the contact between the piston rod and bearing between the bearing and the bung. The detection of the contact gives the information that the drive mechanism is coupled to the bung in such way that further actuation of the drive mechanism would displace the bung in distal direction.

It is possible to send electrical power through the electric conductor e.g. by connecting two sections or ends of the electric conductor to a power source, a voltage or a current flow, wherein the signal feedback of the circuit can be measured, when the conductive connection between the electrical contacts is established as a result of the contact.

In this regard, it is possible to provide, e.g. coat or plate, the drive mechanism at least partly with a conductive material. According to one embodiment of the invention, the electric conductor comprises at least two sections, the section being isolated from each other in a first position of the drive mechanism and the sections being connected to each other in a second position of the drive mechanism. It is, e.g. possible to provide the piston rod with a conductive material, wherein the two sections are separated from each other by isolating material or other suitable means. The bearing can be provided with a conductive material which bridges an isolated gap or a clearance between conductive sections on the piston rod such that the two sections are connected to each other, once the contact between the piston rod and the bearing is made. It is also possible to provide the bung with a conductive material which bridges an isolated gap or a clearance between conductive sections on the bearing such that the two sections are connected to each other, once the contact between the bearing and the bung is made. It is, thereby, possible to detect the end position of the bearing when it reaches the bung. As an alternative, detection of the contact between a component of the drive mechanism and the bung may be based on the interruption of the electric conductor, e.g. by cutting through the electric conductor, or by detecting a change in the electrical resistance of the electric conductor, e.g. by weakening or slabbing the electric conductor.

In one further embodiment of the invention, the bearing is provided with a conductive insert. The insert can be provided in a V-shaped recess, wherein the conductive insert bridges a potential electrical circuit on the piston rod such that transmission of electrical signals is possible when the piston rod contacts the bearing. In another embodiment of the invention, the distal end of the bearing can be provided with a switch. The switch is preferably configured such that the switch is closed by the bung when it approaches and/or abuts the bearing.

It is also possible to make the drive mechanism at least partly of a conductive material. The bearing can at least comprise sections of a conductive surface wherein a conductive connection is established, when the piston rod contacts the bearing.

Preferably, the drive mechanism includes a body surrounding at least a proximal part of the drive mechanism. The electric conductor preferably extends through a proximal opening of said body. This arrangement makes it easy to apply a power source and to attach electrical measurement devices to detect electrical signals when the contact is made, respectively, when the electric circuit is closed or interrupted.

A further embodiment of the drug delivery device may include a lead screw as a piston rod. According to one further embodiment of the invention, the lead screw can be in threaded engagement with a body. Advantageously, the body is at least partly surrounding the lead screw.

In further developing the concept the invention is based on, the lead screw and the body can be connected to each other in such manner that position of the bearing relative to the bung can be regulated by applying torque to the lead screw or to the body. A gap or clearance between the bearing and the bung or between the piston rod and the bearing can be reliably adjusted by rotation of the respective element, providing for a more precise definition of the forward motion relative the drive mechanism.

The electrical conductor may be configured in such manner that it can be connected to an electrical measurement device.

It is preferred, when the cartridge contains a medicament such as insulin.

The drug delivery device can be a disposable injection device. Such devices can be thrown away or recycled after the content of the medicament has been exhausted. However, the present invention is also applicable with re-usable devices designed to replace an emptied cartridge with a filled one after the whole content of the former cartridge has been administered.

An example of a disposable device in which the present invention may be used is given in EP 1 974 761 A2.

The object of the present invention is further achieved by a method for detecting a contact between the drive mechanism and the bung, respectively between the piston rod and the bearing or between the bearing and the bung. The contact is indicated by an electrical signal which is transmitted through the electric conductor. The method includes the step of applying an electrical signal on electric contacts of the electric conductor, displacing the piston rod in direction of the bung and measuring the signal feedback by the electric conductor. The moment, contact between the piston rod and the bearing or between the bearing and the bung is made, an electric circuit constituted by the now joint electric conductor is closed, which enables to send an electrical signal through the formerly interrupted circuit. As an alternative a closed circuit may be interrupted by the bung contacting the drive mechanism.

By applying electric current or the like on the electric conductor, a reliable indication can be achieved that the drive mechanism is fully connected to the bung such that further application of drive force will drive the bung in distal direction. Displacement of the piston rod may be stopped when the signal feedback changes, respectively when the contact between the respective elements is detected. Further priming steps become, therefore, indispensable as the drug delivery device is now in a well prepared state.

As an alternative to the drug delivery device and the method used for detecting a contact between the drive mechanism and the bung, particularly the piston rod and the bearing or the bearing and the bung described herein, the object of the invention can also be solved by using the electric conductor for transmitting a signal wherein, contrary to the above described mechanisms, the conductive connection is not established when the piston rod contacts the bearing or when the bearing contacts the piston rod but wherein a conductive connection is disconnected when the piston rod contacts the bearing or when the bearing contacts the bung. This can e.g. be achieved by means to disconnect an electrical circuit, which can be any suitable switch-releasing means.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta¬decanoyl) human insulin.

Exendin-4 for example means Exendin-4(1-39), a peptide of the sequence H His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 0 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

In the following, the invention will be described by way of an example with reference to the schematic drawing in which.

DETAILED DESCRIPTION

Figure 1:
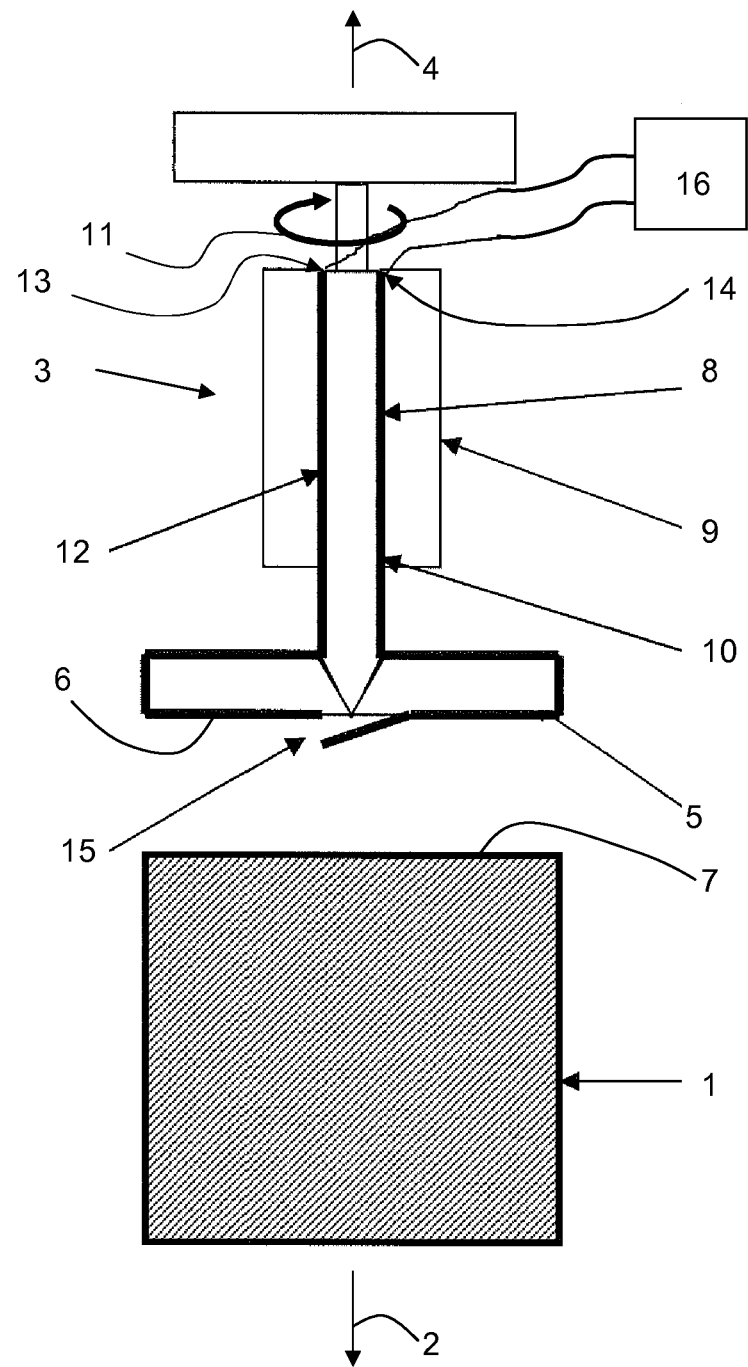
FIG. 1 shows schematically the detection of a contact between a drive mechanism and a bung according to a first embodiment of the invention.

FIG. 1 shows a cartridge bung 1 for expelling a medicament out of a cartridge (not shown) in a distal direction 2. A distal movement of the cartridge bung is induced by a drive mechanism 3 located in proximal direction 4 from the cartridge bung 1. The drive mechanism 3 comprises a bearing 5 with a distal end surface 6 facing a proximal end surface 7 of the cartridge bung 1, which during the assembly of the device is arranged in a distance to the bearing 5 such that a clearance between the bung 1 and the bearing 5 is at hand.

In proximal direction 4 from the bearing 5, a lead screw 8 is arranged, said lead screw 8 being connected to the bearing 5 in such manner, that a movement of the lead screw 8 in distal direction moves the bearing 5 in the same. The lead screw 8 is of an elongated shape and extends from the bearing 5 in proximal direction. A proximal section of the lead screw 8 is surrounded by a body 9, wherein the lead screw 8 and the body 9 are connected to each other via a thread connection 10. The thread connection between the lead screw 8 and the body 9 is configured such that a relative rotation between the elements 8 and 9 results in a translational movement of the lead screw 8 relative to the body 9 in proximal or distal direction. As an example, by applying torque to the lead screw 8 in the direction indicated by arrow 11, the lead screw 8 screws through the body 9 in distal direction thereby displacing the bearing 5 toward the bung 1.

The lead screw 8 and the bearing 5 are provided with an electric conductor 12 which is capable of transmitting an electrical signal. In the shown state, it is not possible to transfer an electrical signal from a first electrical contact 13 of the electric conductor 12 to a second electrical contact 14, as the electric conductor 12 is interrupted at the distal end surface 6 of the bearing 5, the interruption divides the electric conductor in two sections. In order to establish a conductive connection between the electrical contacts 13 and 14 that is capable of transmitting a signal, the bearing 5 is provided with a switch 15 positioned at the distal end surface 6 of the bearing 5. The switch 15 is arranged such to bridge and connect the two sections of the electrical conductor when being closed, in particular when being urged in proximal direction 4.

When the lead screw 8 together with the bearing 5 moves toward the cartridge bung 1, the proximal end surface 7 of the bung 1 will contact the switch 15 and urge the switch 15 in a closed position, in which the connection between the first electrical contact 13 and the second electrical contact 14 is established, thereby closing a potential electric circuit when a power is applied to the contacts 13 and 14.

Electrical measurement means 16 are connected to the electrical contacts 13 and 14 sending signals from one of the contacts 13 or 14 to the other one of the contacts 13 or 14 through the electric conductor 12. However, as long as the bung does not close the switch 15, a signal cannot be transmitted through the electric conductor 12 and can, therefore, not be measured by the measurement means 16. When the bung contacts the bearing 5, the switch 15 is closed and a conductive connection is established wherein an electric signal can be transmitted through the electric conductor 12 from the first electrical contact 13 to the second electrical contact 14. When the signal is received at the second electrical contact 14, it directly indicates that the bearing 5 is in contact with the cartridge bung 1 and that the clearance between the bearing 5 and the bung 1 is eliminated.

Figure 2:
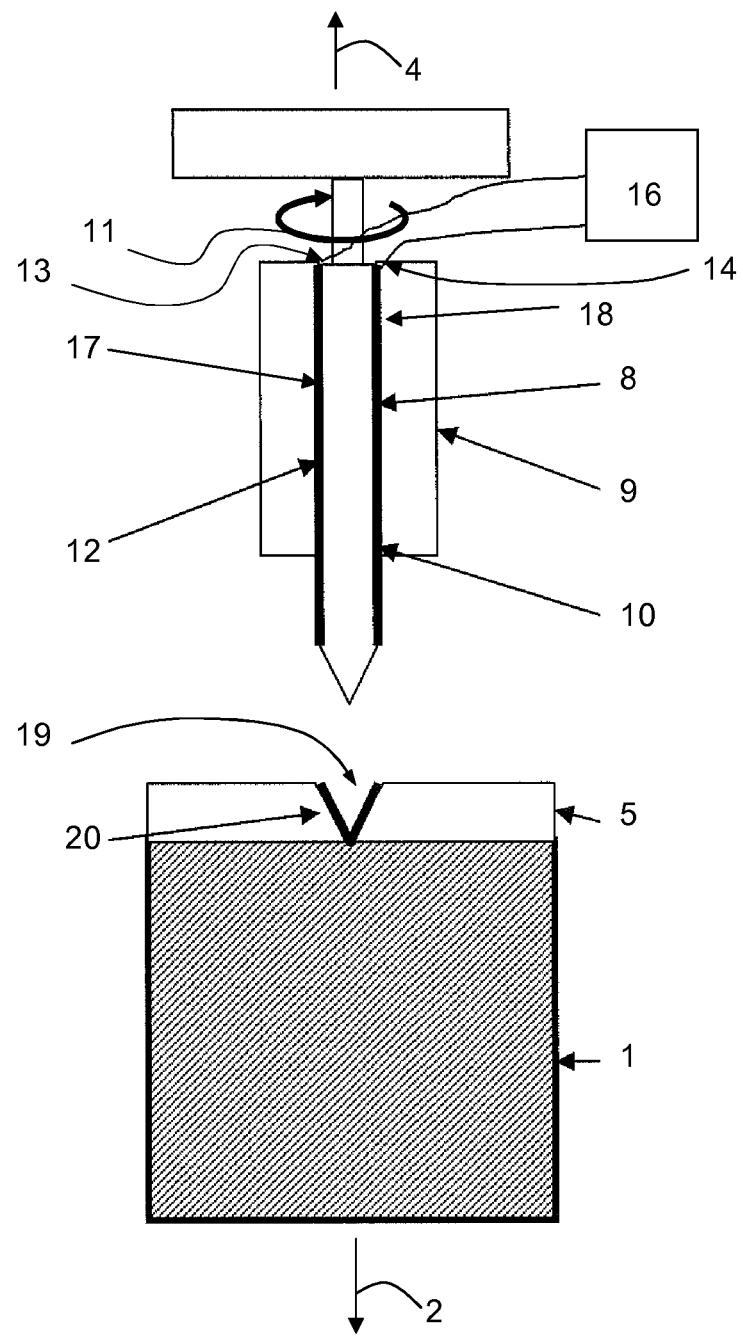
FIG. 2 shows schematically the detection of a contact between a lead screw and a bearing according to a second embodiment of the invention.

In the embodiment shown in FIG. 2, the bearing 5 is provided on the cartridge bung 1 and is in an initial state separated from the lead screw 8. Thus, the bung is not coupled to the drive mechanism in such way that actuation of the drive mechanism will not immediately result in distal movement of the bung 1. The shown arrangement of the bearing 5 on the bung 1 can be done in the assembly process of the drug delivery device. The electric conductor 12 comprises a first section 17 of the electric conductor and a second section 18 of the electric conductor, both sections 17 and 18 being provided on the lead screw 8. Each of the sections 17 and 18 extends from a proximal end of the lead screw 8 to a distal end of the lead screw 8, wherein the two sections 17 and 18 are separated or isolated from each other at the distal end of the lead screw 8 such that a signal emitted from the electrical contact 13 will not arrive at the second electrical contact 14.

The bearing 5 is arranged on the cartridge bung 1 and is provided on its proximal end surface with a V-shaped recess 19. The recess 19 is formed such that it is capable of receiving the distal end of the lead screw 8, which is shaped accordingly and ends in an acute tip. The recess 19 is provided with a conductive insert 20. The shape of the conductive insert 20 is adapted to the V-shape of the recess 19 and to the distal end of the lead screw 8. The proximal ends of the V-shaped conductive insert 20 are regarding their widths configured to connect a distal end of the first section 17 of the electric conductor 12 with the distal end of the second section 18 of the electric conductor 12 in the sense of a bridge.

When the lead screw 8 is displaced in distal direction 2 toward a second position, the distal end of the lead screw 8 will enter the recess 19 whereby the conductive insert 20 connects the first section 17 with the second section 18. An electrical signal that is transmitted into the first electrical contact 13 can now be transmitted through the entire length of the electric conductor 12, in detail through the first section 17 through the conductive insert 20 and through the second section 18 to the second electrical contact 14 and is, therefore, measurable by the electrical measurement means 16. Accordingly, detecting the signal that is transmitted through the signal-transmitting connection directly corresponds to the established contact between the lead screw 8 and the bearing 5. In the same way, it also indicates that the contact between the drive mechanism 3 and the cartridge bung 1 is present.

The invention claimed is:

1. A drug delivery device comprising:
   a cartridge with a movable bung,
   a drive mechanism including a bearing for driving the bung in a distal direction and a lead screw for actuating the bearing, wherein the lead screw being in threaded engagement with a body surrounding at least a proximal part of the drive mechanism and at least partly the lead screw; and
   an electric conductor on the drive mechanism for transmitting an electrical signal,
   wherein the electric conductor extends through a proximal opening of the body and is configured such that a conductive connection is established or interrupted when the lead screw contacts the bearing in a recess of the bearing so that the drive mechanism is in contact with the bung and actuation of the drive mechanism displaces the bung in the distal direction, and
   wherein the bearing is provided with a conductive insert in the recess of the bearing.

2. The drug delivery device according to claim 1, wherein the electric conductor comprises at least two sections, the at least two sections being isolated from each other in a first position of the drive mechanism relative to the bung and the at least two sections being connected to each other in a second position of the drive mechanism relative to the bung.

3. The drug delivery device according to claim 1, wherein at least one component of the drive mechanism is provided with a conductive material.

4. The drug delivery device according to claim 1, wherein a distal end of the bearing is provided with a switch.

5. The drug delivery device according to claim 1, wherein the drive mechanism is at least partly made of conductive material.

6. The drug delivery device according to claim 1, wherein the cartridge contains a medicament.

7. The drug delivery device according to claim 6, wherein the drug delivery device is a disposable injection device.

8. A method for detecting a contact between the drive mechanism and the bung in the drug delivery device according to claim 1, wherein the contact is indicated by presence or absence of an electrical signal transmitted through the electric conductor, the method including the steps of:
   applying an electrical signal on electric contacts of the electric conductor;
   displacing the lead screw in the direction of the bung; and
   taking an electrical measurement of signal feedback provided by the electric conductor.

9. The method according to claim 8, wherein the displacement of the lead screw is stopped upon a change in the signal feedback.

10. The method according to claim 8, wherein the bearing is placed on the bung before displacing the lead screw.

* * * * *

UNITED STATES PATENT AND TRADEMARK OFFICE
CERTIFICATE OF CORRECTION

PATENT NO. : 10,272,204 B2
APPLICATION NO. : 14/421410
DATED : April 30, 2019
INVENTOR(S) : Michael Jugl et al.

Page 1 of 1

It is certified that error appears in the above-identified patent and that said Letters Patent is hereby corrected as shown below:

In the Claims

At Column 10, Claim number 1, Line number 9, delete "wherein" before the phrase "the lead screw being in threaded engagement with a body".

Signed and Sealed this
Twenty-fifth Day of February, 2020

Andrei Iancu
*Director of the United States Patent and Trademark Office*